(12) United States Patent
Kruecker et al.

(10) Patent No.: US 11,185,305 B2
(45) Date of Patent: Nov. 30, 2021

(54) INTERTIAL DEVICE TRACKING SYSTEM AND METHOD OF OPERATION THEREOF

(71) Applicant: KONINKLIJKE PHILIPS N.V., Eindhoven (NL)

(72) Inventors: Jochen Kruecker, Andover, MA (US); Faik Can Meral, Mansfield, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 366 days.

(21) Appl. No.: 16/300,133

(22) PCT Filed: Jun. 27, 2017

(86) PCT No.: PCT/EP2017/065780
§ 371 (c)(1),
(2) Date: Nov. 9, 2018

(87) PCT Pub. No.: WO2018/002004
PCT Pub. Date: Jan. 4, 2018

(65) Prior Publication Data
US 2019/0142374 A1 May 16, 2019

Related U.S. Application Data

(60) Provisional application No. 62/356,622, filed on Jun. 30, 2016.

(51) Int. Cl.
*A61B 8/00* (2006.01)
*A61B 8/12* (2006.01)
(Continued)

(52) U.S. Cl.
CPC .............. *A61B 8/4254* (2013.01); *A61B 8/12* (2013.01); *A61B 34/20* (2016.02);
(Continued)

(58) Field of Classification Search
CPC ......... A61B 8/00; A61B 34/20; A61B 8/4254; A61B 8/12; A61B 2034/2065;
(Continued)

(56) References Cited

U.S. PATENT DOCUMENTS 5,479,926 A * 1/1996 Ustuner .............. G01S 7/52026
348/224.1
5,566,674 A * 10/1996 Weng ................... G01S 7/52046
600/443
(Continued)

FOREIGN PATENT DOCUMENTS

EP 0310045 A1 4/1989
WO 9953838 A1 10/1999
(Continued)

*Primary Examiner* — Oommen Jacob (57) ABSTRACT

A tracking system for ultrasound imaging includes an imaging probe which acquires ultrasound image information including a plurality of ultrasound image frames; an inertial measurement unit coupled to the imaging probe and which synchronously acquires tracking information including a plurality of tracking frames indicative of motion of the imaging probe; and a controller. The controller is configured to obtain the ultrasound image information for at least two of the plurality of ultrasound image frames from the plurality of ultrasound imaging frames, and determine a similarity value based upon a comparison of the at least two ultrasound image frames. The controller is configured to compute whether the similarity value ($C_{frame}$) is less than a similarity threshold value ($C_{thresh}$), and select first or second pose estimation methods, each different from each other, based upon results of the computation of whether the similarity value ($C_{frame}$) is less than the similarity threshold value ($C_{thresh}$).

20 Claims, 5 Drawing Sheets

(51) Int. Cl.
*A61B 34/20* (2016.01)
*A61B 90/00* (2016.01)

(52) U.S. Cl.
CPC ............ *A61B 2034/2048* (2016.02); *A61B 2034/2063* (2016.02); *A61B 2034/2065* (2016.02); *A61B 2090/0818* (2016.02); *A61B 2090/378* (2016.02)

(58) Field of Classification Search
CPC .... A61B 2034/2048; A61B 2090/0818; A61B 2090/378; A61B 2034/2063; A61B 2034/3048; A61B 8/463; A61B 8/483; A61B 8/0833; G01S 7/52074; G01S 15/8979; G01S 7/5206; G01S 7/52068; G01S 7/52073; G01S 15/52; G01S 15/88; G01S 15/8993; G06T 7/223; G06T 7/238; G06T 7/246; G06T 2207/10016; G06T 2207/10068; G06T 2207/30196
See application file for complete search history.

(56) References Cited

U.S. PATENT DOCUMENTS

| | | | | |
|---|---|---|---|---|
| 5,575,286 A * | 11/1996 | Weng | ............ | A61B 8/0866 600/425 |
| 5,602,891 A * | 2/1997 | Pearlman | ............ | A61B 6/463 250/363.01 |
| 5,655,535 A * | 8/1997 | Friemel | ............ | A61B 8/0866 128/916 |
| 5,776,066 A * | 7/1998 | Nock | ............ | A61B 8/08 600/443 |
| 5,844,612 A * | 12/1998 | Israelsen | ............ | H04N 19/172 375/240.14 |
| 5,873,830 A * | 2/1999 | Hossack | ............ | G01S 7/52074 600/447 |
| 5,876,342 A * | 3/1999 | Chen | ............ | G06T 7/254 600/443 |
| 6,083,168 A * | 7/2000 | Hossack | ............ | G01S 7/52046 600/443 |
| 6,122,538 A | 9/2000 | Sliwa et al. | | |
| 6,162,174 A * | 12/2000 | Friemel | ............ | G01S 7/52026 600/447 |
| 6,272,253 B1 * | 8/2001 | Bannon | ............ | G06T 9/007 382/236 |
| 6,474,159 B1 * | 11/2002 | Foxlin | ............ | G01C 21/12 73/488 |
| 6,589,176 B2 | 7/2003 | Jago et al. | | |
| 6,638,221 B2 * | 10/2003 | Abe | ............ | A61B 8/14 600/437 |
| 7,583,275 B2 * | 9/2009 | Neumann | ............ | G06T 17/00 345/419 |
| 7,840,040 B2 * | 11/2010 | Wilcox | ............ | A61B 8/4483 382/128 |
| 8,594,927 B2 * | 11/2013 | Louis | ............ | G01C 21/005 701/445 |
| 8,686,892 B2 * | 4/2014 | McCleary | ............ | G01S 13/9027 342/25 R |
| 8,913,792 B2 * | 12/2014 | BenHimane | ............ | G06T 7/246 382/103 |
| 8,951,194 B2 * | 2/2015 | Shin | ............ | G06T 7/248 600/437 |
| 9,024,972 B1 * | 5/2015 | Bronder | ............ | G06F 3/012 345/633 |
| 9,186,087 B2 * | 11/2015 | Liao | ............ | G16H 50/30 |
| 9,224,060 B1 | 12/2015 | Ramaswamy | | |
| 9,232,924 B2 * | 1/2016 | Liu | ............ | A61B 6/4441 |
| 9,324,151 B2 * | 4/2016 | Snavely | ............ | G06T 7/74 |
| 9,341,483 B2 * | 5/2016 | Chao | ............ | G01C 21/005 |
| 9,525,862 B2 * | 12/2016 | Benhimane | ............ | G06T 7/246 |
| 9,607,388 B2 * | 3/2017 | Lin | ............ | H04N 13/282 |
| 9,677,890 B2 * | 6/2017 | Yang | ............ | G01S 5/0252 |
| 9,697,609 B2 * | 7/2017 | Kim | ............ | G06K 9/00342 |
| 9,754,419 B2 * | 9/2017 | Petrovskaya | ............ | G06K 9/00671 |
| 10,162,362 B2 * | 12/2018 | Tsai | ............ | G01S 5/16 |
| 10,588,604 B2 * | 3/2020 | Xie | ............ | A61B 8/4245 |
| 2003/0105401 A1 * | 6/2003 | Jago | ............ | A61B 8/4254 600/443 |
| 2005/0085728 A1 | 4/2005 | Fukuda | | |
| 2006/0173305 A1 * | 8/2006 | Asafusa | ............ | G01S 15/8961 600/437 |
| 2006/0293592 A1 | 12/2006 | Jensen | | |
| 2007/0049824 A1 * | 3/2007 | Konofagou | ............ | G01S 7/52042 600/437 |
| 2008/0187896 A1 * | 8/2008 | Savitsky | ............ | G09B 23/288 434/272 |
| 2008/0262345 A1 * | 10/2008 | Fichtinger | ............ | A61B 90/39 600/426 |
| 2010/0331855 A1 * | 12/2010 | Zhao | ............ | A61B 34/30 606/130 |
| 2013/0016185 A1 | 1/2013 | Stolka et al. | | |
| 2013/0296707 A1 | 11/2013 | Anthony et al. | | |
| 2014/0195149 A1 * | 7/2014 | Yang | ............ | G01C 21/005 701/445 |
| 2014/0243671 A1 | 8/2014 | Holl et al. | | |
| 2014/0355825 A1 * | 12/2014 | Kim | ............ | G06K 9/00369 382/103 |
| 2015/0185018 A1 | 7/2015 | Hesch et al. | | |
| 2015/0219767 A1 * | 8/2015 | Humphreys | ............ | G01S 19/48 342/357.26 |
| 2015/0320514 A1 | 11/2015 | Ahn et al. | | |
| 2016/0113730 A1 | 4/2016 | Lightcap et al. | | |
| 2016/0191887 A1 * | 6/2016 | Casas | ............ | A61B 34/20 348/47 |
| 2019/0142374 A1 * | 5/2019 | Kruecker | ............ | A61B 34/20 600/462 |

FOREIGN PATENT DOCUMENTS

WO 03047433 A1 6/2003
WO 2014018983 A1 1/2014

* cited by examiner

INTERTIAL DEVICE TRACKING SYSTEM AND METHOD OF OPERATION THEREOF

CROSS-REFERENCE TO PRIOR APPLICATIONS

This application is the U.S. National Phase application under 35 U.S.C. § 371 of International Application Serial No. PCT/EP2017/065780, filed on Jun. 27, 2017, which claims the benefit of U.S. Patent Application No. 62/356,622, filed on Jun. 30, 2016. This application is hereby incorporated by reference herein.

FIELD OF THE PRESENT SYSTEM

The present system relates to a navigation system which employs inertial-based location methods to determine velocity and pose of a medical imaging device and, more particularly, to a medical navigation system which employs inertial-based tracking methods and selectively employs image-based tracking methods to track medical imaging devices, and methods of operation thereof.

BACKGROUND OF THE PRESENT SYSTEM

In medical procedures (hereinafter procedures for the sake of clarity), real-time information about the spatial position and orientation (i.e., the "pose") of a medical device is often required. Typically, such information is obtained using optical, electro-magnetic, mechanical or ultrasound-based tracking systems. Such systems are expensive and can require significant setup time and effort. Typically, motion-based inertial tracking devices experience bias which can lead to tracking inaccuracies. For example, bias in acceleration and rotational velocity estimates can lead to inaccurate velocity, position, and rotational position estimates when using motion-based inertial tracking systems.

When using motion-based inertial tracking system for medical device tracking, the pose of the medical device may not always be tracked accurately over extended periods of time. The requirements for accuracy may vary by procedure and/or medical device. For example, depending upon procedure, when the device to be tracked is an imaging device (e.g. an ultrasound probe), the requirements for the accuracy of the device position tracking may be less stringent. In this case, it may be desirable to provide position tracking while implementing a less complex position-tracking system which may conserve system resources and reduce cost. Thus, embodiments of the present system may overcome these and other disadvantages of conventional tracking-systems and methods.

SUMMARY OF THE PRESENT SYSTEM

The system(s), device(s), method(s), arrangements(s), user interface(s), computer program(s), processes, etc. (hereinafter each of which will be referred to as system, unless the context indicates otherwise), described herein address problems in prior art systems. Embodiments of the present system may provide a system and method for acquiring image-based information and employing this image-based information to correct bias errors in inertial-based sensors of imaging devices for position tracking. Embodiments of the present system may be ideally suited for use in imaging systems such as ultrasound imaging systems. In accordance with embodiments of the present system, there is disclosed a tracking system for ultrasound imaging, comprising an imaging probe which acquires ultrasound image information including a plurality of ultrasound image frames; an inertial measurement unit coupled to the imaging probe and which synchronously acquires tracking information including a plurality of tracking frames indicative of motion of the imaging probe; and a controller. The controller is configured to obtain the ultrasound image information for at least two of the plurality of ultrasound image frames from the plurality of ultrasound imaging frames, and determine a similarity value based upon a comparison of the at least two ultrasound image frames, where the similarity value may be a value of a similarity metric, the similarity metric including at least one of correlation, mutual information, and sum of squared differences.

The controller is configured to compute whether the similarity value ($C_{frame}$) is less than a similarity threshold value ($C_{thresh}$), and select first or second pose estimation methods, each being different from each other, based upon the results of the computation of whether the similarity value ($C_{frame}$) is less than the similarity threshold value ($C_{thresh}$).

The controller may also be configured to select the first pose estimating method when it is determined that the similarity value ($C_{frame}$) is less than the similarity threshold value ($C_{thresh}$), where the first pose estimating method determines pose by integrating the tracking information from the IMU and storing the result in a memory of the system. Further, the controller may also be configured to select the second pose estimating method when it is determined that the similarity value ($C_{frame}$) is not less than the similarity threshold value ($C_{thresh}$), where the second pose estimating method employs image frames obtained from ultrasound information and determines pose based upon an image-based bias correction of integrated tracking information. The tracking system further includes a rendering device, where the controller determines pose in accordance with the selected pose estimation method and renders the determined pose on the rendering device.

In another embodiment, a method for tracking an ultrasound probe is performed by at least one controller, and comprised acts of:
  acquiring ultrasound image information including a plurality of ultrasound image frames from the ultrasound probe;
  synchronously acquiring tracking information including a plurality of tracking frames indicative of motion of the ultrasound probe from an inertial measurement unit coupled to the ultrasound probe;
  determining a similarity value based upon a comparison of at least two ultrasound image frames of the plurality of ultrasound image frames;
  computing whether the similarity value ($C_{frame}$) is less than a similarity threshold value ($C_{thresh}$); and
  selecting first or second pose estimation methods each different from each other based upon the results of the computation of whether the similarity value ($C_{frame}$) less than the similarity frame, threshold value ($C_{thresh}$).

The method of claim 9, further comprises an act of selecting the first pose estimating method when it is determined that the similarity value ($C_{frame}$) is less than the similarity threshold value ($C_{thresh}$), where the first pose estimating method determines pose by integrating the tracking information from the IMU, and thereafter stores the results in a memory of the system. In addition, the method, further comprises an act of selecting the second pose estimating method when it is determined that the similarity value ($C_{frame}$) is not less than the similarity threshold value ($C_{thresh}$), where the second pose estimating method further comprises an act of determining pose based upon an image-based bias correction of integrated tracking information. In addition, the method include an act of determining pose in accordance with the selected pose estimation method and rendering the determined pose on a rendering device.

In another embodiment, a non-transitory computer readable medium comprises computer instructions which, when executed by a processor, configure the processor to perform the acts of:

acquiring ultrasound image information including a plurality of ultrasound image frames from the ultrasound probe;

synchronously acquiring tracking information including a plurality of tracking frames indicative of motion of the ultrasound probe from an inertial measurement unit coupled to the ultrasound probe;

determining a similarity value based upon a comparison of at least two ultrasound image frames of the plurality of ultrasound image frames;

computing whether the similarity value ($C_{frame}$) is less than a similarity threshold value ($C_{thresh}$); and selecting first or second pose estimation methods each different from each other based upon the results of the computation of whether the similarity value ($C_{frame}$) less than the similarity frame, threshold value ($C_{thresh}$).

Additional computer instructions which, when executed by a processor, configure the processor to perform the acts of selecting the first pose estimating method when it is determined that the similarity value ($C_{frame}$) is less than the similarity threshold value ($C_{thresh}$); selecting the second pose estimating method when it is determined that the similarity value ($C_{frame}$) is not less than the similarity threshold value ($C_{thresh}$); and determining pose in accordance with the selected pose estimation method and rendering the determined pose on a rendering device.

The first pose estimating method determines pose by integrating the tracking information from the IMU, and thereafter stores the results in a memory of the system. Further, the second pose estimating method further comprises an act of determining pose based upon an image-based bias correction of integrated tracking information.

BRIEF DESCRIPTION OF THE DRAWINGS

The present invention is explained in further detail in the following exemplary embodiments and with reference to the figures, where identical or similar elements are partly indicated by the same or similar reference numerals, and the features of various exemplary embodiments being combinable. In the drawings.

DETAILED DESCRIPTION OF THE PRESENT SYSTEM

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

Figure 1:
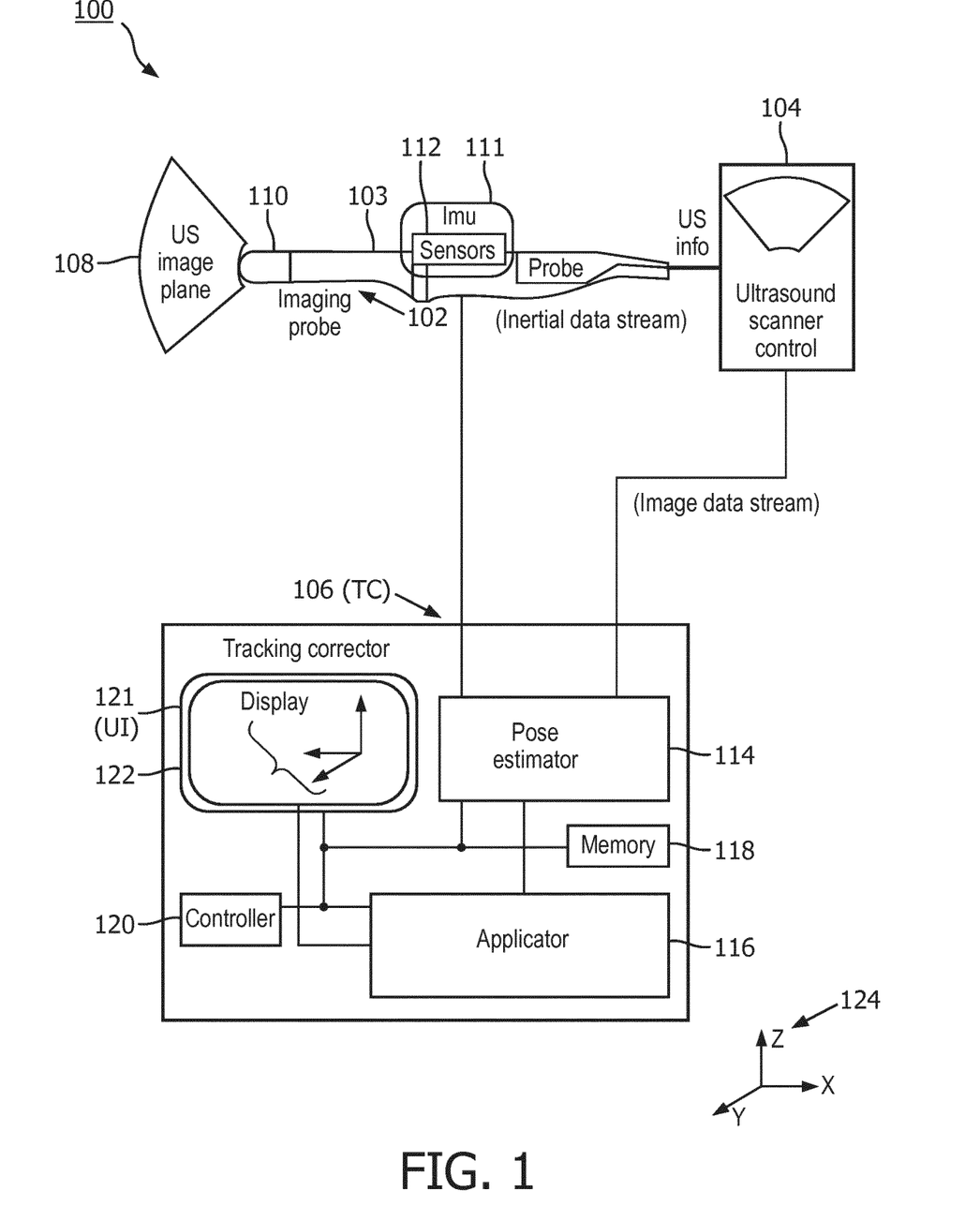
FIG. 1 shows a schematic block diagram of a portion of a tracking system (hereinafter system for the sake of clarity) operating in accordance with embodiments of the present system.

FIG. 1 shows a schematic block diagram of a portion of a tracking system 100 (hereinafter system 100 for the sake of clarity) operating in accordance with embodiments of the present system. The system 100 may include one or more of a medical imaging device (MID) such as an ultrasound probe 102 (hereinafter probe for the sake of clarity unless the context indicates otherwise), an ultrasound scanner control 104, an inertial measurement unit (IMU) 111, and a tracking corrector 106 communicatively coupled to each other via any suitable wired and/or wireless methods. Further, it is envisioned that one or more of the imaging probe 102, the ultrasound scanner control 104, and the tracking corrector 106 may be formed integrally with another of the imaging probe 102, the ultrasound scanner control 104, and the tracking corrector 106, as may be desired.

The IMU 111 may be coupled to the MID such as the probe 102 and may include sensors 112. For example, the IMU 111 may be releasably or fixedly coupled to the probe 102 as may be desired. The IMU may include a coupler or may be shaped to couple to the probe 102.

The sensors 112 may include one or more inertial measurement sensors, such as accelerometers and/or gyroscopes, to determine linear acceleration or rotational velocity, respectively, of the probe 102, to form corresponding sensor information, and to provide this sensor information as an inertial data stream (InDS) to the tracking corrector 106 for further processing. It is envisioned that the sensors 112 may include any suitable sensors such as miniature electromechanical (MEMS) inertial tracking sensors, and/or the like. The sensors 112 may have accuracy levels on the order of milli-g (i.e., 10 mm/s$^2$) for linear acceleration, and a few degrees per hour bias stability for rotation, and may be low cost sensors. A workflow and algorithm for using low-cost-sensors combined with image-based position estimates, along with determined reliability values, are described in U.S. Provisional Patent Application No. 62/266,733 entitled "System and Method for Medical Device Tracking" and filed on Dec. 14, 2015, which is incorporated herein by reference in its entirety.

The sensor information may include one or more of linear acceleration and rotational velocity information generated by the accelerometers and the gyroscopes, respectively, and may be formed into corresponding tracking frames in time. More particularly, the accelerometers may sense linear acceleration along one or more axes (e.g., x, y, and z axes as shown by arrow 124) and generate corresponding linear acceleration information, and the gyroscopes may sense rotation about one or more axes (e.g., x, y, and z axes) and generate corresponding rotational velocity information. The sensor information may be included within the InDS and the InDS may be provided to a pose estimator 114 of the tracking corrector 106 for further processing. Time information (e.g., acquisition time) may be included within the sensor information or may be separate from the sensor information and included within the InDS. Thus, the InDS may include time information indicating an acquisition time which may be used for synchronization with ultrasound information obtained from the image data stream as may be desired.

The sensors 112 may be situated at a single location or may be distributed throughout the IMU 111 as may be desired. For example, the sensors 112 may be located integrally with each other or may be located separately from each other. Further, the sensors 112 may be integrated with, e.g., located inside the probe 102, and/or may be outside, e.g., attached to the probe 102. In one embodiment, the sensors 112 are positioned as close to the image plane (i.e., as close to the tip of the probe 102) as possible, in order to minimize any errors introduced by extrapolating the motion/rotation (which was measured at the sensor position) to the image plane position. Thus, according to an embodiment, the sensors 112 may be positioned in the probe 102 within 20 mm of the transducer array 110.

The probe 102 may include one or more of a transducer array 110 and a body 103. The transducer array 110 may include one or more ultrasound transducers configured in a desired order so as to transmit ultrasound waves and acquire ultrasound information of at least one ultrasound image plane such as an ultrasound image plane 108. Although the MID is shown to include the probe 102, it is envisioned that other types of MIDs may be used to acquire medical imaging data as may be desired. For example, other types of MIDs may include X-ray imaging devices or nuclear imaging devices such as Gamma-cameras.

The ultrasound information may include in any suitable format such as an analog and/or digital format and may be transmitted to the ultrasound scanner control 104 for further processing. In accordance with embodiments of the present system, the ultrasound information may include corresponding time information indicating an acquisition time which may be used for synchronization as may be desired.

The probe 102 may include any suitable ultrasound probe for a procedure being performed. For example, in the present embodiments, the probe 102 may be assumed to include at least one of an endo-cavity probe, endo-bronchial probe, cardiac probe, laparoscopic ultrasound probe, abdominal probe, small-parts or general imaging probe, and the like, including a multi-channel ultrasound probe, which may obtain ultrasound image information for constructing images of a region-of-interest (ROI) which may include one or more ultrasound image planes, such as the ultrasound image plane 108. The probe may be capable of 1-dimensional (1D), 2D, and/or 3D imaging.

The ultrasound scanner control 104 may receive the ultrasound information and process this information to form corresponding ultrasound image information which may include ultrasound image frame information (UIFIs) for a plurality of image frames. This ultrasound image information may then be provided within the image data stream to the pose estimator unit 114 for further processing. The ultrasound image information may include time information indicating an acquisition time as may be desired.

The tracking corrector (TC) 106 may include one or more of a controller 120, the pose estimation unit 114, an application unit 116, a memory 118, a user interface (UI) 121 with which a user may interface with, and a display 122, one or more of which may be formed integrally with, or separately from, each other.

The controller 120 may control the overall operation of the system 100 and may communicate with one or more of the probe 102, the IMU 111, the ultrasound scanner control 104, the pose estimator 114, the application unit 116, the memory 118, the UI 121, and/or the display 122 using any suitable wired or wireless communication methods. The functions of one or more of the pose estimator 114 and the applicator 116 may be integrated within controller 120 as may be desired. Further, the controller 120 may control operation of the ultrasound scanner control 104 and/or the probe 102.

The memory 118 may include any suitable non-volatile memory in which information such as operating instructions, information generated by the system, user inputs and/or settings, historical information, operating settings and/or parameters, identification information, user information, patient information, etc., may be stored.

The UI 121 may include any suitable user interface which may allow for input (e.g., user input) and output such as rendering information for the convenience of the user, such as the display 122 which may display graphical user interfaces (GUIs) generated by the system and/or other image information. Accordingly, the UI may include a speaker (SPK), the display 122 (e.g., a touch-screen display, etc.), a haptic device (e.g., vibrators, etc.) with which to render information for the convenience of the user.

The pose estimator 114 may obtain the inertial data stream (InDS) from the IMU 111 and the image data stream from the ultrasound scanner 104, and process information within these streams in accordance with embodiments of the present system to determine pose estimates which may be provided to the applicator 116 for further processing.

Generally, the pose estimates may be determined by integrating the acceleration information from the sensors 112 (e.g., obtained from the inertial data stream) to obtain velocity, and integrating again to obtain spatial position; further angular velocity data from the gyroscopes are integrated once to obtain heading (rotational position). However, any small error, bias or drift in acceleration and angular velocity may be accumulative over time and, thus, in the pose estimate, leading to deteriorating pose estimates over time. Accordingly, the pose estimator 114 may determine a type of displacement (e.g., large, small, no, etc.) and thereafter determine the pose estimate in accordance with settings for the type of displacement.

A method to analyze the inertial data stream and the image data stream as performed by the pose estimator 114 and the applicator 116 under the control of the controller 120 of the tracking corrector 106 in accordance with embodiments of the present system may be described with reference to FIG. 2 below. However, in brief, the pose estimator 114 may receive one or more of the image data stream and the inertial data stream and determine a pose information related to the determined pose of the probe 102.

Referring back to FIG. 1, the applicator 116 may receive the determined pose information from the pose estimator 114 and process this pose information in accordance with system settings and output results. The system settings may be set and/or reset by the system and/or user, and may be stored in a memory of the system for later use. For example, the system settings may be set such that the applicator 116 may generate a graphical user interface (GUI) including a graphical depiction of the MID such as the ultrasound probe 102, and provide this content to the UI 121 which may then render this information on a suitable rendering device of the system, such as on the display 122 of the system 100 for the convenience of the user. Similarly, the content may include other information such as audible information which may be rendered on a suitable rendering device of the system such as on a speaker of the system. Likewise haptic information may be rendered using a vibrator of the system. Thus, for example, the system may determine whether a current pose of the probe 102 indicates that the probe 102 is at a desired location, and when it is determined that the current pose of the probe 102 indicates that the probe 102 is at a desired location, the controller 120 may output a signal to drive a haptic device of the system to inform a user (e.g., via a vibratory feedback) that the probe 102 is at the desired location. The controller 120 may further determine guidance information to place the probe 102 in the desired position and render this information on a rendering device of the system such as the display 122. Thus, the applicator 116 may obtain the pose information and generate corresponding guidance information to, for example, control a location of the ultrasound probe 102 and/or inform a user of an actual and/or desired location of the ultrasound probe 102 so that the user may move the ultrasound to the desired location. For example, the guidance information may include a color-coded bar which indicates the distance (length of bar) and out-of-plane direction (toward front/back of current image plane, indicated by the bar having different colors, such as green/blue) from the current image plane to the desired image plane. It is further envisioned that the applicator 116 may obtain the pose information and fuse ultrasound image information obtained from the ultrasound probe 102 with previously-obtained ultrasound image information using any suitable method such as a fusing method provided by, for example, the UroNav™ (Philips Invivo, Gainesville, Fla.) fusion biopsy system or the like.

Figure 2:
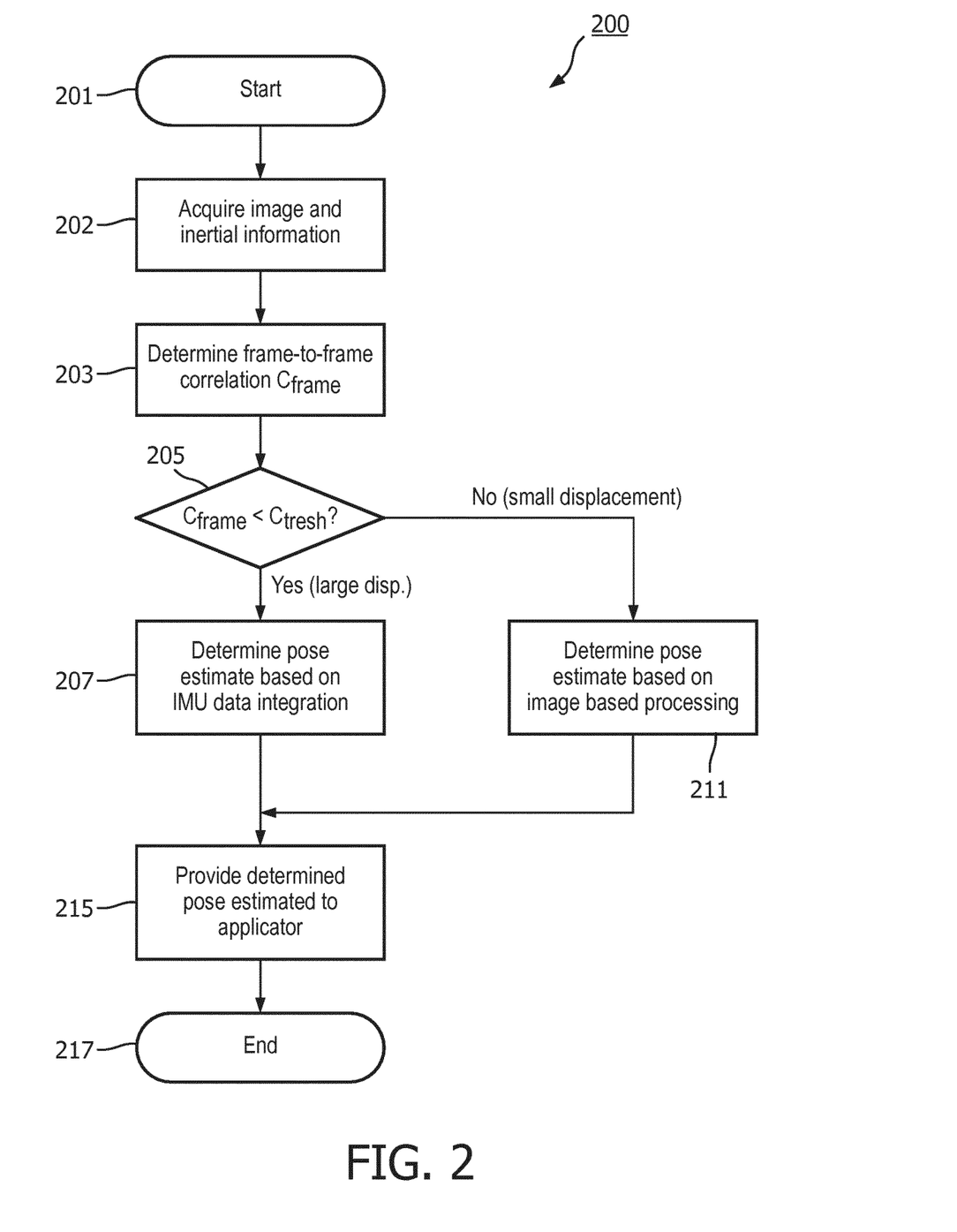
FIG. 2 shows a functional flow diagram performed by a process in accordance with embodiments of the present system.

FIG. 2 shows a functional flow diagram performed by a process 200 in accordance with embodiments of the present system. The process 200 may be performed using one or more processors, computers, controllers, etc., communicating over a network and may obtain information from, and/or store information to one or more memories which may be local and/or remote from each other. The process 200 may include one of more of the following acts. In accordance with embodiments of the present system, the acts of process 200 may be performed using one or more suitable coordinate registration systems operating in accordance with embodiments of the present system. Further, one or more of these acts may be combined and/or separated into sub-acts, as desired. Further, one or more of these acts may be skipped depending upon settings. For the sake of clarity, the process may be described with reference to a single probe such as an ultrasound probe. However, without limitation, it should be understood that the process may employ a plurality of probes each of which may be include a separate workflow. Also for the sake of clarity, in the illustrative embodiment shown in FIG. 2, process 200, correlation ($C_{frame}$) between at least two frames is used as a similarity metric, however, without limitation, it should be understood that other measures of similarity may be used instead of, or in addition to correlation, such as mutual information, normalized mutual information, sum of squared differences, correlation ratio, correlation coefficient, and/or other measures of similarity. Similarly, instead of, or in addition to computing correlation for at least last two frames ($C_{frame}$), other similarity metrics may be computed for the at least last two frames ($C_{frame}$) and compared with a similarity metric threshold ($C_{thresh}$).

In operation, the process 200 may start during act 201 and then proceed to act 202. During act 202, the system may obtain ultrasound image information acquired by the probe in real time. The ultrasound information may include a plurality of image frames acquired by the probe and may be included within an image data stream. Accordingly, these image frames may be obtained through an analysis of the image data stream. Simultaneously with the ultrasound image acquisition, the system may acquire inertial information which may include acceleration information (e.g., linear and rotational) from an IMU of the system that may be coupled to, or otherwise part of, the probe. After completing act 202, the process may continue to act 203.

During act 203, the system may determine a frame-to-frame similarity metric, such as a frame-to-frame correlation ($C_{frame}$) for two or more adjacent image frames of the ultrasound image information. These frames may be adjacent to each other in time or may be situated over a certain interval of time (e.g., a running window of time). After completing act 203, the process may continue to act 205.

During act 205, the process may determine whether the $C_{frame}$ is less than a correlation threshold $C_{thresh}$ (i.e., whether $C_{frame} < C_{thresh}$). Accordingly, the process may compare $C_{frame}$ to $C_{thresh}$ and if it is determined that $C_{frame}$ is less than $C_{thresh}$ (e.g., indicative of a large displacement of the probe) the process may continue to act 207. However, if it is determined that $C_{frame}$ is not less than $C_{thresh}$ (e.g., $C_{frame}$ is greater than or equal to $C_{thresh}$, which is indicative of a small displacement), the process may continue to act 211. With regard to $C_{thresh}$, this value may be set to any suitable value such as 0.9 in the present embodiments. However, other values or ranges of values are also envisioned.

During act 207, the system may determine a pose estimate based at least upon integrated IMU data of tracking information obtained from the IMU (e.g., tracking data). Accordingly, the system may perform an IMU data integration process to integrate the IMU data (between previous and present bias correction time points) and determine a pose estimate (which may be defined as a current pose or pose estimate) based at least upon this integrated IMU data and a previous pose. After completing act 207, the process may continue to act 215.

During act 211, the process may determine a pose estimate based at least upon image-based processing methods as may be applied to the ultrasound image information acquired by the ultrasound probe. During this act, the system may employ image-based processing (such as frame-to-frame correlation and out-of-plane correlation) to estimate a current velocity of the ultrasound probe. Then, the system may compare the change since the last bias correction (e.g., between previous and present bias correction time points) in this current velocity estimate (obtained by the image-based processing) with a change in velocity estimate provided by the integrated IMU data between previous and present bias correction time points, and use the difference to estimate an acceleration bias of the IMU as indicated by the tracking data. The system may then apply the bias correction retrospectively to all time points since the last bias correction (e.g., from m to (m−1)) and update the current pose estimate accordingly. The current pose estimate may then be provided to the application unit as a current pose.

A special subset of small displacements may occur when the probe is stationary. If this is the case, then the frame-to-frame correlations are highest (between identical images except micron level tissue movements and ultrasound scanner system noise) and the resulting velocity estimation (e.g., determined via image analysis) is essentially zero. After completing act 211, the process may continue to act 215.

During act 215, the process may transmit the pose estimate to the applicator (e.g., the applicator 116) for further processing as may be described elsewhere in this application and may thereafter continue to act 217 where it may end.

With regard to bias correction, the bias correction may be triggered to occur automatically when the ultrasound probe is determined to be stopped or slowed (e.g., below a certain velocity threshold), or may be triggered manually (e.g., by a user as will be discussed below, etc.). For example, bias correction may be triggered manually by a user when the ultrasound probe is stationary and/or immediately prior to an ultrasound probe motion sequence that requires high tracking accuracy. Additionally, the applicator may monitor a period of time since a last motion correction (e.g., a bias correction) has been applied, and when it is determined that the period of time since the last motion correction is greater than a motion correction time threshold ($T_{thresh}$), the applicator may generate and render a message requesting the user to slow down or stop the motion so that motion correction may be applied. In other words, when it is determined that a predetermined period of time since a previous motion correction has elapsed (e.g., motion correction has not been applied for a predetermined period of time (e.g., 20 seconds, etc.)), the system may inform a user (e.g., by rendering the message requesting the user to slow down or stop the motion so that motion correction may be applied) to slow down probe motion and thereafter preform motion correction once the frame-to-frame correlation $C_{frame}$ increases to reach and/or become greater than the correlation threshold $C_{thresh}$. When the user follows the request slow down or stop and indeed slows down or stops the ultrasound probe motion, then the frame-frame correlation $C_{frame}$ increases to reach and/or become greater $C_{thresh}$. It should be noted that act 205 is again performed where it is checked that $C_{frame}$ increased to reach and/or exceed $C_{thresh}$, and act 211 is performed to determine pose estimates based on the actually acquired imaging data following the request to user and the user act of slowing down or stopping the motion of the ultrasound probe.

Figure 3:
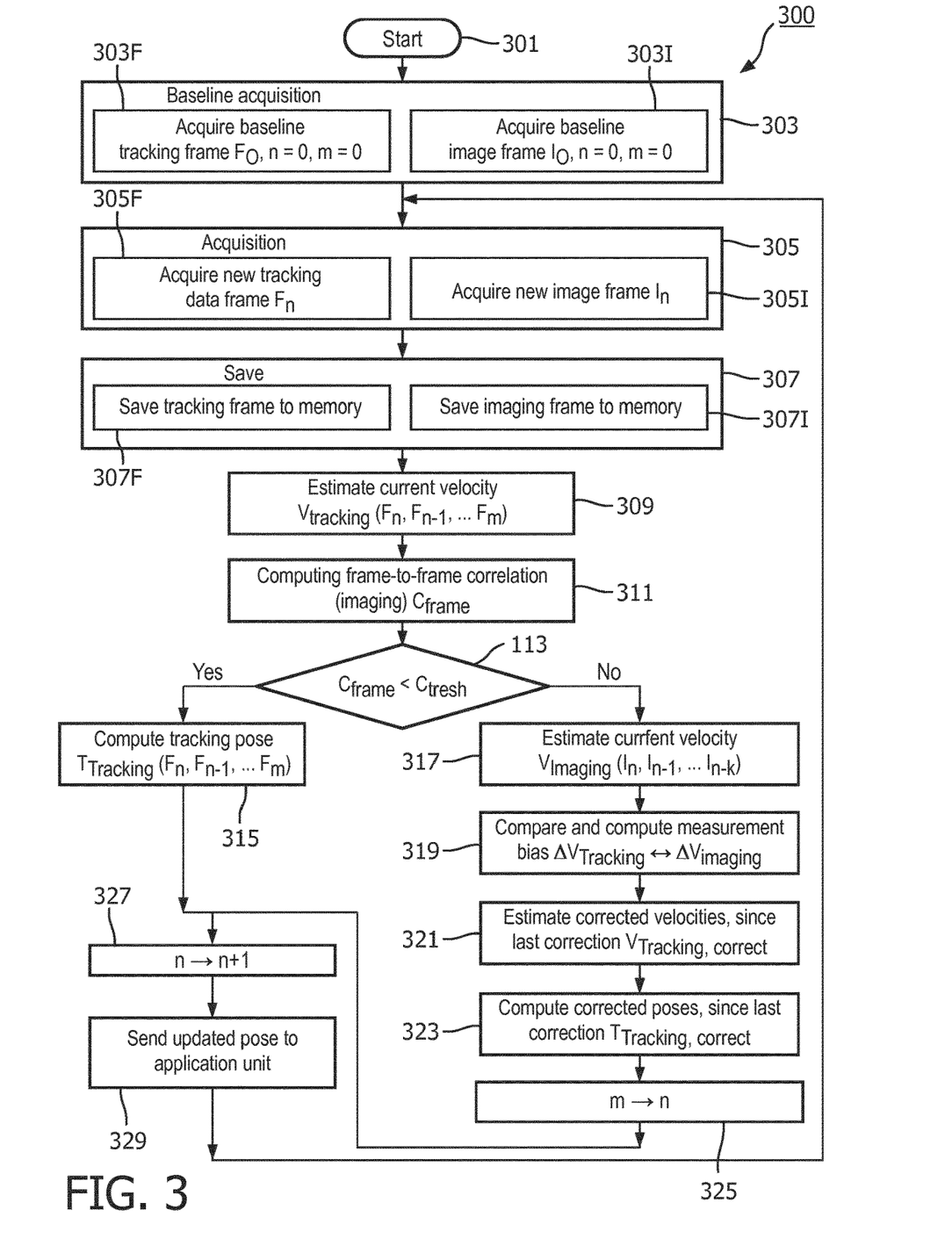
FIG. 3 shows a functional flow diagram performed by a process in accordance with embodiments of the present system.

A method for performing image-based bias correction in the pose estimation unit will now be discussed with reference to FIG. 3 which shows a functional flow diagram performed by a process 300 in accordance with embodiments of the present system. The process 300 may be performed using one or more processors, computers, controllers, etc., communicating over a network and may obtain information from, and/or store information to one or more memories which may be local and/or remote from each other. The process 300 may include one of more of the following acts. In accordance with embodiments of the present system, the acts of process 300 may be performed using one or more suitable coordinate registration systems operating in accordance with embodiments of the present system. Further, one or more of these acts may be combined and/or separated into sub-acts, as desired. Further, one or more of these acts may be skipped depending upon settings. For the sake of clarity, the process may be described with reference to a single probe such as an ultrasound probe. However, without limitation, it should be understood that the process may employ a plurality of probes each of which may be include a separate workflow such as a sub-workflow. In operation, the process may start during act 301 and then proceed to act 303. Further, information determined by the system may be stored in a memory of the system for later use.

During act 303, the system may perform a baseline acquisition to simultaneously acquire baseline tracking and image frames from each of the IMU and the probe (e.g., an ultrasound probe). For example, the system may acquire a baseline tracking frame ($F_n$, n=0, m=0) from an IMU during sub-act 303F and may simultaneously capture a baseline image frame ($I_n$, n=0, m=0) from the probe (e.g., directly or via an ultrasound scanner) during act 303I, where $F_n$ denotes a tracking frame (e.g., from IMU data), $I_n$ denotes an image frame (e.g., an ultrasound image frame from the ultrasound probe 102), wherein n denotes an index (which may start at 0 for the initial frame), and m denotes a bias correction iteration and may be initially set to the value of n, which is 0 during the current act. Thus, the baseline tracking frame may be known as $F_0$ and the baseline image frame (e.g., ultrasound image frame) may be known as $I_0$. The absolute baseline probe velocity is assumed to be 0 (probe stationary) and the probe pose at baseline is assumed to be at the origin of the coordinate system (i.e. position x=0 in a 1-dimensional example, or x=(0,0,0) in a 3-dimensional coordinate system). All subsequent position and velocity estimates are estimates of position/velocity change relative to this baseline, or relative to the last bias correction point as detailed below. After the baseline acquisitions, the system may advance a count of index n such that n=n+1.

Simultaneous acquisition of tracking frames and imaging frames may be initiated from the application unit at a known initial pose (e.g., at origin of a selected coordinate system) when the probe is stationary. Accordingly, the system may render information to inform a user to place the ultrasound probe in a desired location (e.g., in a holder) for initialization. However, it is also envisioned that the system may detect when the probe is placed in a desired position (e.g., using sensors in a base, etc.) which may provide information to indicate that the probe is positioned correctly within the base and that an initialization process may begin. It is further envisioned that the user may initiate the initialization process manually when the probe is place in a desired pose, such as when it is placed in a stand, or when it is manually held in a stationary position at the beginning of a desired scan sequence. After completing act 303, the process may continue to act 305.

During act 305, the system may perform an acquisition to simultaneously acquire current (e.g., new) frames from each of the IMU and the ultrasound probe in real time. For example, the system may acquire a current baseline tracking frame ($F_n$) from the IMU during sub-act 305F and may simultaneously capture a current image frame ($I_n$) from the ultrasound scanner during sub-act 305I. After completing act 305, the process may continue to act 307.

During act 307, the system may save the frames acquired during acts 303 and 305 in a memory of the system for later use. For example, the system may save the acquired tracking frames ($F_n$) in a tracking frame memory during sub-act 307F and may save the acquired imaging frames ($I_n$) during sub-act 307I. The system may further store meta information, such as time of acquisition, probe and/or acquisition parameters, etc., with corresponding tracking and imaging frames. After completing act 307, the system may continue to act 309.

During act 309, the system may estimate a current tracking-based velocity of the probe. Thus, the system may determine an inertial-tracking-based velocity $v_{Tracking}$ ($F_n$, $F_{n-1}$, ... $F_m$) of the probe for each tracking frame $F_n$ over m frames. Accordingly, the system may obtain the acquired tracking frames ($F_n$) from the tracking frame memory and process this information to determine a current velocity (e.g., a tracking-based velocity) of the probe, by integrating the inertial acceleration data over time for all frames since the last correction, resulting in the tracking-based velocity change since the last correction. The absolute velocity estimate is obtained by adding the velocity at the last correction time to the velocity change estimates. Thus, if n=1, and m=0, the system may determine $v_{Tracking}$ ($F_1$, $F_0$). After completing act 309, the system may continue to act 311.

During act 311, the system may compute a frame-to-frame correlation ($C_{frame}$) for the acquired imaging frames ($I_n$). Accordingly, the system may determine a correlation between adjacent imaging frames such as a correlation between a current $n^{th}$ imaging frame ($I_n$) and a previous imaging frame ($I_{n-1}$) which correspond with index (e.g., n) of the image frames that were used to determine the current tracking-based velocity during act 309. Illustratively, up to k=10 frames are correlated to increase the robustness of the image-based velocity estimate. Further, the frames used for correlation may be adjacent in time. In an embodiment, an image quality metric may be employed to select which frames have sufficient image information to allow image-based velocity estimates. For example, ultrasound shadowing can obscure parts of the image. If too much of an image is "dark" (i.e., shadowed), then this image should not be used to attempt calculation of probe velocity. The image quality metric could thus measure average image brightness and only use frames that show sufficient brightness, such as a brightness above a preselected/predetermined brightness threshold. After completing act 311, the process may continue to act 313.

During act 313, the process may determine whether $C_{frame}$ is less than a correlation threshold value ($C_{thresh}$). Accordingly, if it is determined that $C_{frame}$ is less than $C_{thresh}$, the process may continue to act 315 and determine a current tracking-based pose based upon an IMU information integration method as will be discussed below. However, if it is determined that $C_{frame}$ is not less than $C_{thresh}$ (e.g., $C_{frame}$ is equal to or greater than $C_{thresh}$), the process may continue to act 317 and determine current pose based upon image-based processing method of image frames (In) from the imaging probe 102 corresponding to and/or obtained in real-time simultaneously with tracking frames ($F_n$) from the IMU, as will be discussed below. This image-based processing method may employ a bias correction mode as may be discussed elsewhere.

It is envisioned that $C_{thresh}$ may be set by the system and/or user and may be stored in a memory of the system and/or obtained when desired. In accordance with embodiments of the present system, $C_{thresh}$ may be set equal to 0.90. However, other values are also envisioned. Further, a plurality of correlation threshold values ($C_{thresh(x)}$), where x is an integer, also envisioned. For example, a first correlation threshold value ($C_{thresh(1)}$) may be set equal to $C_{thresh}$=0.90, and a second correlation threshold value ($C_{thresh(2)}$) may be set equal to 0.93. These two values may then be used for comparison purposes as may be described elsewhere.

During act 315, the process may determine a tracking-based pose $T_{Tracking}$($F_n$, $F_{n-1}$, ... $F_m$) for the probe based upon an integration of the estimated inertial tracking-based velocity $v_{Tracking}$ ($F_n$, $F_{n-1}$, ... $F_m$) determined during act 309. More particularly, the process may determine the tracking-based pose of the probe based upon an IMU data integration method which may integrate over the estimated inertial tracking-based velocity $v_{Tracking}$ ($F_n$, $F_{n-1}$, ... $F_m$) to determine the tracking-based pose $T_{Tracking}$ ($F_n$, $F_{n-1}$, ... $F_m$). In this method, bias correction may not be applied because the low correlation ($C_{frame}$<$C_{thresh}$) suggest that any image-based correction attempt would be less accurate than estimating velocity and pose directly from the inertial data. The pose change (since the last correction time) estimates are obtained by integrating over (adding) all velocity estimates $v_{Tracking}$ ($F_n$, $F_{n-1}$, ... $F_m$) to get the pose change since the last correction time, and adding the pose at the last correction time to get the absolute pose (i.e., pose change since baseline).

Thus, tracking data may be integrated to estimate the probe velocity, position and orientation, where $v_{Tracking}$ and $T_{Tracking}$ are the (inertial) tracking-based velocity and pose changes respectively, since a last bias correction (e.g., which may be a previous correction instant), which may be denoted by subscript m as will be discussed elsewhere. After completing act 315, the system may continue to act 327. As described in connection with acts 303 and 309, all estimates are estimates of the pose/velocity change relative to the last correction point. By adding the pose/velocity at the last correction point, the overall velocity/pose change since baseline is obtained, which is the absolute pose/velocity estimate since the pose/velocity were both zero by definition at baseline, e.g., at origin of the coordinate system.

During acts 317 through 325, the system may employ bias correction to correct the tracking pose to determine a corrected tracking pose which may then be set as the current pose.

More particularly, during act 317, the system may determine an (estimated) image-based velocity $v_{Imaging}$($I_n$, $I_{n-1}$, ... $I_{n-k}$) using up to k number (where k is an integer<=10, for example) of retrospective imaging frames ($I_n$, $I_{n-1}$, ... $I_{n-k}$). In particular, the system may only use the 2 most recent image frames ($I_n$ and $I_{n-1}$) to determine the current velocity. This act may be performed using any suitable imaging-based processing methods such as digital signal processing (DSP) methods or the like. During this act, the system may determine velocity based upon a difference of adjacent (in time) image frames. For example, the system may further identify landmarks within the image frames and may thereafter measure a shift of these landmarks to determine velocity, if any. After completing act 317, the system may continue to act 319.

During act 319, the system may compute a measurement bias (B). Accordingly, the process may determine a change between estimated tracking-based velocity changes since the last correction, and image-based velocity changes since the last correction (at frame m). For example, the change in the imaging-based velocity may be represented as $\Delta v_{imaging}$, with $\Delta v_{imaging} = v_{imaging,n} - v_{imaging,m}$, and the change in tracking-based velocity may be represented as $\Delta v_{imaging} = v_{imaging,n} - v_{imaging,m}$. The process may then determine the bias (B) based upon a difference between $\Delta v_{imaging}$ to $\Delta v_{tracking}$. Thus, the bias (B) may be based upon the difference of image- and tracking-based velocity changes. If probe motion in d dimensions is considered (d=1, 2 or 3), the bias can be described as a d-dimensional vector. After completing act 319, the process may continue to act 321.

During act 321, the process may determine corrected tracking-based velocities for all estimates since the last correction $v_{Tracking,\ correct}$ for the probe. Accordingly, the process may determine the tracking-based velocities $v_{Tracking,\ correct}$ by applying the measurement bias (B) or a fraction thereof to the previously determined tracking-based velocity $v_{Tracking}$ ($F_n, F_{n-1}, \ldots F_m$) information which may have been previously stored in the memory. For example, the process may use linear interpolation to apply a fraction of the bias to each previously stored velocity estimate since the last correction, such that zero bias is applied (added to) the velocity estimate at the last correction point (at frame m), the full bias B is applied to the current velocity estimate (at frame n), and a fraction of the bias (j−m)/(n−m)*B is applied to all previously stored velocity estimates for frames $F_j$ with j=m ... n, i.e. for all frames between the last correction point and the current frame. The determined corrected tracking-based velocities $v_{Tracking,\ correct}$ for the probe may be referred to as estimated corrected tracking-based velocities. After completing act 321, the process may continue to act 323.

During act 323, the process may determine a corrected tracking-based pose $T_{Tracking,\ correct}$ for the probe. The process may determine the corrected tracking-based probe $T_{Tracking,\ correct}$ based upon an integration of determined corrected tracking-based velocities $v_{Tracking,\ correct}$ for the probe determined during act 321. More particularly, the process may determine the corrected tracking-based pose $T_{Tracking,\ correct}$ based upon an IMU data integration method which may integrate over the corrected tracking-based velocities $v_{Tracking,\ correct}$ to determine the corrected tracking-based pose $T_{Tracking,\ correct}$. This integration may be similar to the integration performed during act 315 above. The corrected tracking-based pose $T_{Tracking,\ correct}$ for the probe may then be set as the tracking-based pose $T_{Trackin}$. After completing act 323, the process may continue to act 325. Thus, during acts 317-323, the system may determine pose based upon an image-based bias correction of the integrated tracking information.

During act 325, the process may set m=n, thus identifying the current frame n as the frame with the last bias correction. After completing act 325, the process may continue to act 327.

During act 327, the system may increment a value of n (e.g., n=n+1) and may continue to act 329.

During act 329, the system may send the updated pose information to an application unit for further processing and rendering, such as aiding a user to determine location and/or orientation of the probe, for surgical guidance (e.g., move probe to left, right, etc.), and/or to fuse information from the ultrasound probe with other medical imaging information (e.g., magnetic-resonance imaging (MRI) scan information, X-ray computed tomography (CT) scan information, etc.) an/or to render this fused information, as may be desired and/or determined by a corresponding use and/or settings. After completing act 329, the system may repeat act 305. Further, it is envisioned that the process may end or otherwise be suspended when desired such as when a user or the system requests to end or suspend the process, respectively.

During the process 300, it is envisioned that once the correction is applied, data stored in the memory can be deleted to clear space for incoming frames. However, it is envisioned that this data may be stored in the memory for a plurality of correction cycles or longer for a more complex estimation of the bias (linear, higher order polynomial, etc. . . . ) as may be desired. Thus, the correction cycle may employ data from a plurality of correction cycles (e.g., acts 317 through 325) as may be desired.

A method to determine bias (B) as illustrated with respect to act 319 will now be discussed in further detail with respect to a one-dimensional (1D) translational case (e.g. an ultrasound probe translating in the lateral direction only, with an IMU tracking sensor measuring lateral acceleration) will now be discussed in further detail. A frame-to-frame image correlation may be performed to detect instances where the ultrasound probe may be stationary, which may result in very high correlation (e.g. greater than 0.98). An image-based velocity estimate of $v_{imaging} = 0$ m/s may be assumed for these stationary instances.

From one stationary instant to the next one, the change in the linear velocity of the probe may be written as $$v_{imaging}(t_2) - v_{imaging}(t_1) \int_{t_1}^{t_2} a_{x,actual} dt = 0 \qquad \text{Eq. (1),}$$

where $t_1$ and $t_2$ are two time points with image-based zero velocity estimates, and $a_{x,actual}$ is the acceleration of the probe. In the absence of IMU tracking measurement bias, the above expression is the same and equal for measured tracking data $$v_{tracking}(t_2) - v_{tracking}(t_1) \int_{t_1}^{t_2} a_{x,measured} dt = 0 \qquad \text{Eq. (2)}$$

If the measurement bias is written as $a_{x,measured} = a_{x,actual} + a_{x,bias}$, then the expression in Eq. (2) may becomes $$\int_{t_1}^{t_2} (a_{x,actual} + a_{x,bias}) dt = v_{tracking}(t_2) - v_{tracking}(t_1) = v_{imaging}(t_2) - v_{imaging}(t_1) + v_{bias}. \qquad \text{Eq. (3)}$$

Therefore it can be concluded that when the IMU acceleration data is integrated from $t_1$ to $t_2$ to obtain tracking based velocity estimates, any non-zero velocity estimation may be due to the tracking measurement bias.

It may be possible to estimate $a_{bias}$ assuming that it is constant between $t_1$ and $t_2$, and correct for it in the retrospective measurements such that the tracker based velocity change is equal to the image based estimate of the velocity change between $t_1$ and $t_2$. Thus, $$a_{bias\ estimate} = \frac{[v_{tracking}(t_2) - v_{tracking}(t_1)] - [v_{imaging}(t_2) - v_{imaging}(t_1)]}{t_2 - t_1}. \qquad \text{Eq. (4)}$$

Test Results

Figure 4A:
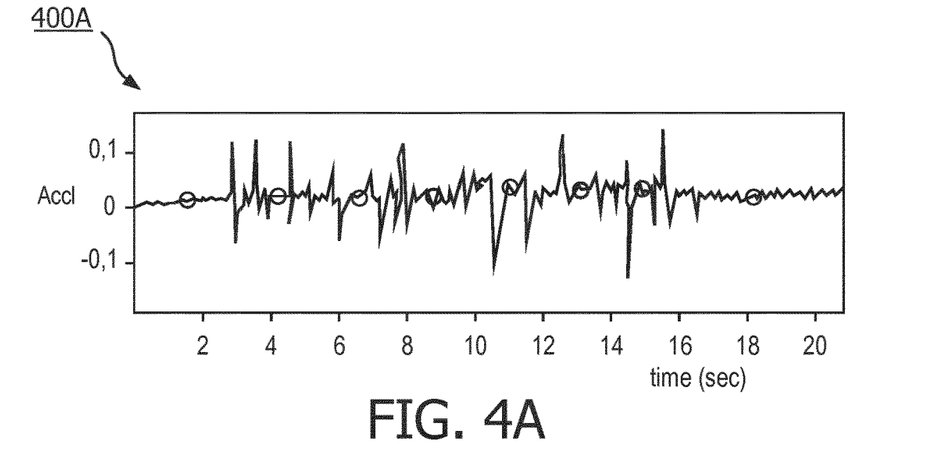
FIG. 4A shows a graph of accelerometer-measured acceleration (accl) vs. time data of a probe (e.g., an ultrasound probe) on a 1-dimensional trajectory, with stationary probe instances detected through image correlation indicated by circle (o) markers, in accordance with embodiments of the present system.
Figure 4B:
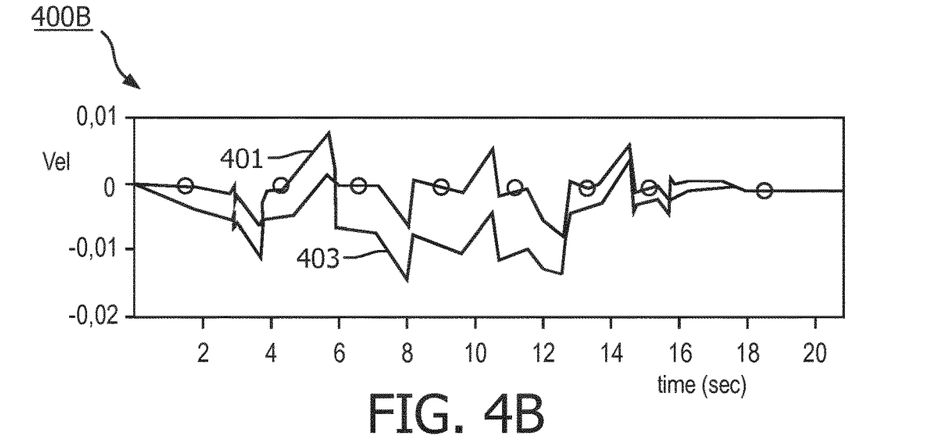
FIG. 4B shows a graph of accelerometer-derived uncorrected (403) and image-based-corrected (401) velocity (Vel) vs time data, along with circle (o) markers indicating stationary probe instances detected through image correlation, determined in accordance with embodiments of the present system.
Figure 4C:
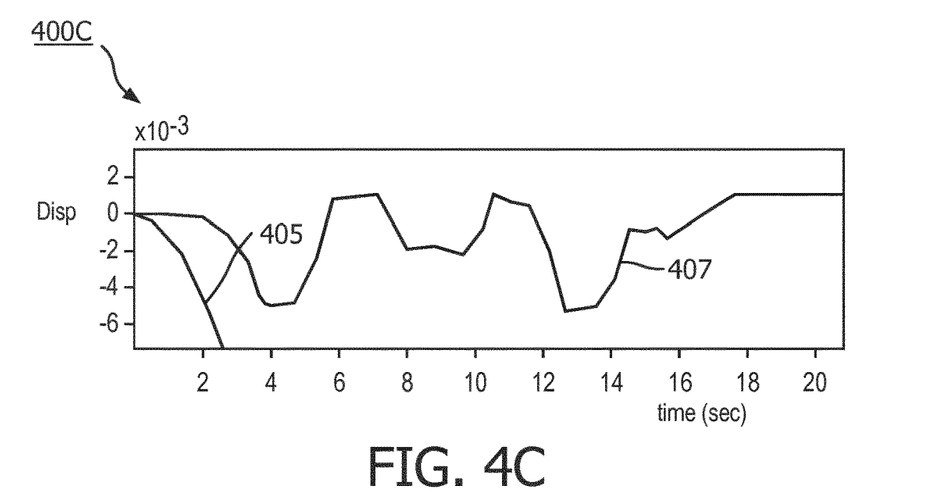
FIG. 4C shows a graph of accelerometer-derived probe displacement estimates without (405) and with (407) the image-based corrections determined in accordance with embodiments of the present system.

IMU acceleration measurements and results for a 1D demonstration case for an imaging probe with and without bias correction performed in accordance with embodiments of the present system will now be described with reference to FIGS. 4A through 4C where:

FIG. 4A shows a graph 400A of accelerometer-measured acceleration (accl) vs. time data, namely, time in seconds t (sec), of a probe (e.g., an ultrasound probe) on a 1-dimensional trajectory, with stationary probe instances detected through image correlation indicated by circle (o) markers, in accordance with embodiments of the present system;

FIG. 4B shows a graph 400B of accelerometer-derived uncorrected (403) and image-based-corrected (401) velocity (Vel) vs time data t (sec), along with circle (o) markers indicating stationary probe instances detected through image correlation, determined in accordance with embodiments of the present system;

FIG. 4C shows a graph 400C of accelerometer-derived probe displacement estimates (Disp) vs time data t (sec), without (405) and with (407) the image-based corrections determined in accordance with embodiments of the present system With reference to graph 400B, an effect of bias upon uncorrected velocity estimates is seen as a drift relative to expected velocities (line 403). However, this drift may be eliminated using bias correction as illustrated by line 401. With reference to graph 400C, without correction, the displacement estimates quickly move to unrealistically large values (line 405), which may be generally unacceptable for application in medical imaging and image guidance. However, with the correction these displacement estimates (line 407) may remain near the expected values.

Although the above-described methods are shown for 1D and zero velocity, the above-described methods may be generalized to three-dimensional (3D) and/or non-zero velocity estimates, i.e. $\Delta v_{imaging} = v_{imaging}(t_2) - v_{imaging}(t_1)$, which is compared with $\Delta v_{tracking} = v_{tracking}(t_2) - v_{tracking}(t_1) - \int_{t_1}^{t_2} a_{x,measured} dt$. Additionally, the constant bias assumption can be replaced with any other (e.g. linear, parabolic, etc. . . . ) time variant bias characteristics and similar corrections can be applied over the course of multiple image based velocity estimation points.

During an initial setup and/or when desired, the system may render information to prompt the user to scan slowly and/or keep the probe stationary if no such slow/no motion is detected after some scan time (e.g. 20 seconds, however other periods of time are also envisioned). This may provide for calibration when desired. It is further envisioned that when the motion of the probe motion is stationary and/or below a velocity threshold for a period of time (e.g. 5 seconds, however other periods of time are also envisioned), image-based velocity estimates may be used to calculate and update the pose.

It is further envisioned that image-based velocity estimates may be based on multiple recent frames stored in a memory of the system.

Figure 5:
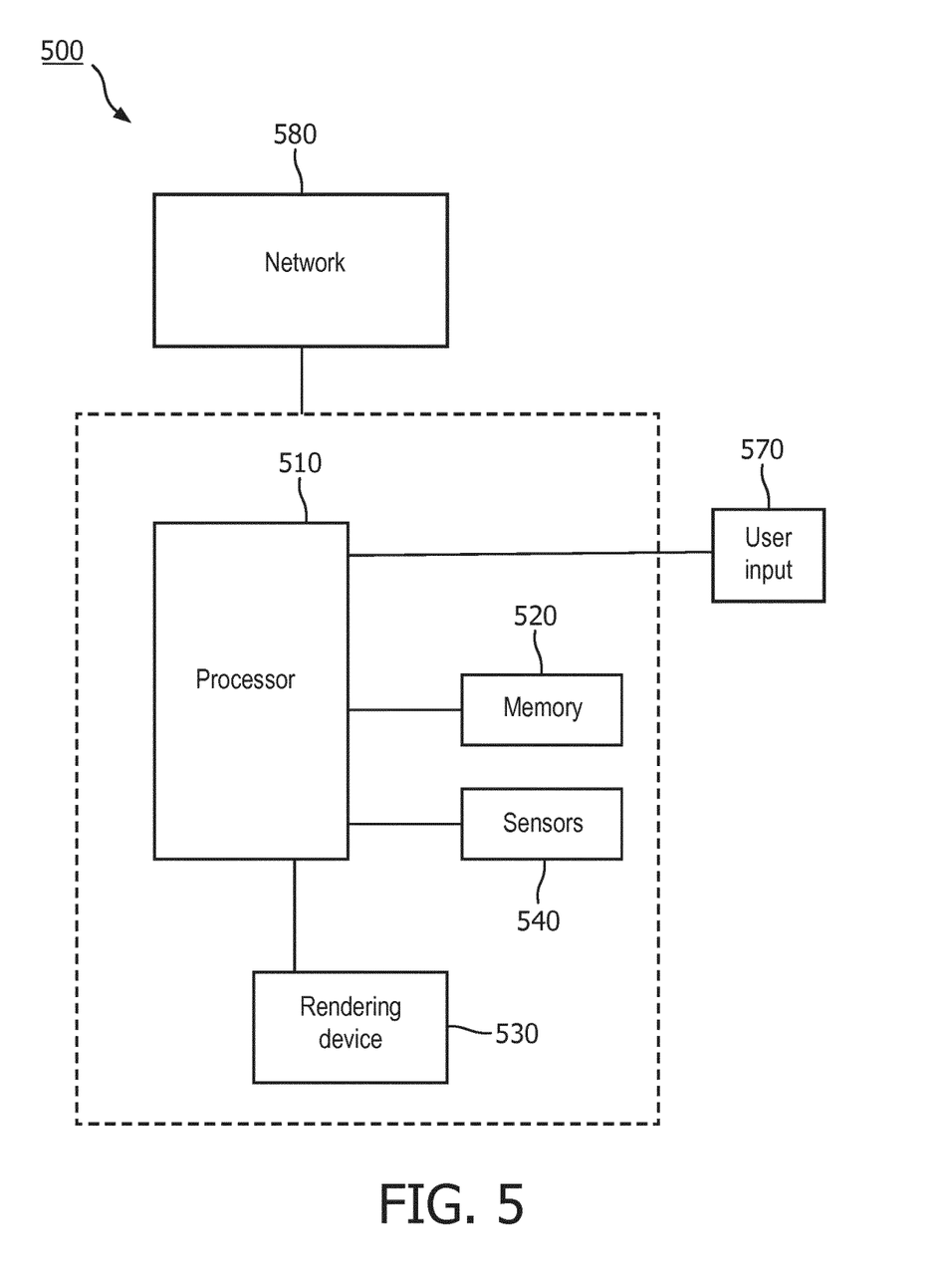
FIG. 5 shows a portion of a system in accordance with embodiments of the present system.

FIG. 5 shows a portion of a system 500 in accordance with embodiments of the present system. For example, a portion of the present system may include a processor 510 (e.g., a controller) operationally coupled to a memory 520, a user interface (UI) including a rendering device such as a display 530, sensors 540, and a user input device 570. The memory 520 may be any type of device for storing application data as well as other data related to the described operation. The application data and other data are received by the processor 510 for configuring (e.g., programming) the processor 510 to perform operation acts in accordance with the present system. The processor 510 so configured becomes a special purpose machine particularly suited for performing in accordance with embodiments of the present system.

The operation acts may include configuring a system by, for example, an inertial tracking system in accordance with system settings.

The processor 510 may determine velocity and/or pose (e.g., position and/or orientation) information received from a medical imaging probe such as an ultrasound probe including an IMU coupled thereto. The processor 510 may further determine guidance information based upon difference information based upon a difference of a desired location and/or pose and the actual location and/or pose of the ultrasound probe. The processor 510, thereof may process received signals such as sensor information, transform these signals to determine velocity, location, and/or orientation information (e.g., related to the probe), and may generate content which may include image information (e.g., still or video images (e.g., video ultrasound information)), data, and/or graphs that may be rendered on, for example, a UI of the system such as on the display 530, a speaker, etc. The content may include image information as may be generated by a medical imaging system of the present system and/or may include guidance information (e.g., move right, left, arrows, etc.) to guide a user during a procedure. Further, the content may then be stored in a memory of the system such as the memory 520 for later use. The processor 510 may further register a location of the probe and/or fuse the content obtained from the probe (e.g., the ultrasound information) with information obtained from other medical imaging systems such as MRI and/or computer-aided tomography (CAT), X-ray, etc. systems. Thus, operation acts may include requesting, providing, and/or rendering of content. The processor 510 may render the content such as video information on a UI of the system such as a display of the system.

The user input 570 may include a keyboard, a mouse, a trackball, or other device, such as a touch-sensitive display, which may be stand alone or part of a system, such as part of a personal computer, a personal digital assistant (PDA), a mobile phone (e.g., a smart phone), a monitor, a smart or dumb terminal or other device for communicating with the processor 510 via any operable link such as a wired and/or wireless communication link. The user input device 570 may be operable for interacting with the processor 510 including enabling interaction within a UI as described herein. Clearly the processor 510, the memory 520, display 530, and/or user input device 570 may all or partly be a portion of a computer system or other device such as a client and/or server.

The methods of the present system are particularly suited to be carried out by a computer software program, such program containing modules corresponding to one or more of the individual steps or acts described and/or envisioned by the present system. Such program may of course be embodied in a non-transitory computer-readable medium, such as an integrated chip, a peripheral device or memory, such as the memory 520 or other memory coupled to the processor 510.

The program and/or program portions contained in the memory 520 may configure the processor 510 to implement the methods, operational acts, and functions disclosed herein. The memories may be distributed, for example between the clients and/or servers, or local, and the processor 510, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 510. With this definition, information accessible through a network is still within the memory, for instance, because the processor 510 may retrieve the information from the network for operation in accordance with the present system.

The processor 510 is operable for providing control signals and/or performing operations in response to input signals from the user input device 570 as well as in response to other devices of a network and executing instructions stored in the memory 520. The processor 510 may include one or more of a microprocessor, an application-specific or general-use integrated circuit(s), a logic device, etc. Further, the processor 510 may be a dedicated processor for performing in accordance with the present system or may be a general-purpose processor wherein only one of many functions operates for performing in accordance with the present system. The processor 510 may operate utilizing a program portion, multiple program segments, or may be a hardware device utilizing a dedicated or multi-purpose integrated circuit. Embodiments of the present system may provide imaging methods to acquire and/or reconstruct images. Suitable applications may include imaging systems such as ultrasound. However, without limitation it should be understood that embodiments of the present system may further include imaging systems such as MRI, computer-aided tomography (CAT), optical, X-ray, and/or combinations thereof. Further, embodiments of the present system may be ideally suited for surgical interventional techniques which may generate and render image and/or sensor information from one or more imaging systems (e.g., ultrasound, CAT scans, MRI, X-ray etc.) having different coordinate systems in real-time with a unified coordinate system. The system may determine pose of the probe and may register the probe and/or image information obtained from the probe with these other systems. Accordingly, the system may determine velocity and/or pose of the probe for registration with these other systems.

Accordingly, embodiments of the present system may process image-based information to correct bias errors in inertial sensors that may be attached to imaging devices for position tracking. This may reduce the need for highly-complex and expensive inertial or non-inertial sensors (such as electro-magnetic tracking sensors) and may allow the implementation of simple, low-cost inertial sensors. It is envisioned that embodiments of the present system may be ideal for various image-based inertial guidance systems. For example, and without limitation, it is envisioned that embodiments of the present system may be employed with ultrasound image guidance systems for prostate biopsy and the like.

Without limitation, it is envisioned that embodiments of the present system may be used for tracking poses of various medical probes such as for tracking a three-dimensional (3D) pose of an imaging probe. In particular, embodiments of the present system may be used for tracking the 3D pose of an ultrasound imaging probe during procedures that may require the fusion of ultrasound image data with pre-acquired data. Such systems may include a US/MRI-fusion-guided prostate biopsy system (e.g., see, UroNav™ system by Philips Invivo, Gainesville, Fla.). It is also envisioned that embodiments of the present system may be used for the general fusion of US with prior 3D imaging (CT, MR, cone-beam CT etc.), or diagnostic exams in which an extended field-of-view (FOV) is to be covered or reconstructed.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, any section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

What is claimed is:

1. A tracking system for ultrasound imaging, comprising:
   an imaging probe which acquires ultrasound image information including a plurality of ultrasound image frames;
   an inertial measurement unit coupled to the imaging probe and which synchronously acquires tracking information including a plurality of tracking frames indicative of motion of the imaging probe; and
   a controller which is configured to:
   obtain the ultrasound image information for at least two of the plurality of ultrasound image frames from the plurality of ultrasound imaging frames,
   determine a similarity value based upon a comparison of the at least two ultrasound image frames,
   compute whether the similarity value ($C_{frame}$) is less than a similarity threshold value ($C_{thresh}$), and
   select first or second pose estimation methods for the imaging probe each different from each other-based upon the results of the computation of whether the similarity value ($C_{frame}$) is less than the similarity threshold value ($C_{thresh}$).

2. The tracking system of claim 1, wherein the controller selects the first pose estimating method when it is determined that the similarity value ($C_{frame}$) is less than the similarity threshold value ($C_{thresh}$).

3. The tracking system of claim 2, wherein the first pose estimating method determines pose by integrating the tracking information from the IMU and storing the result in a memory of the system.

4. The tracking system of claim 2, wherein the controller selects the second pose estimating method when it is determined that the similarity value ($C_{frame}$) is not less than the similarity threshold value ($C_{thresh}$).

5. The tracking system of claim 4, wherein the second pose estimating method determines pose based upon an image-based bias correction of integrated tracking information.

6. The tracking system of claim 5, wherein the second pose estimating is an image-based processing method that employs image frames obtained from ultrasound information.

7. The tracking system of claim 1, further comprising a rendering device wherein the controller determines pose in accordance with the selected pose estimation method and renders the determined pose on the rendering device.

8. The tracking system of claim 1, wherein the similarity value is a value of a similarity metric, the similarity metric including at least one of correlation, correlation coefficient, mutual information, normalized mutual information, correlation ratio, and sum of squared differences.

9. A method for tracking an ultrasound probe, the method being performed by at least one controller and comprising acts of:
acquiring ultrasound image information including a plurality of ultrasound image frames from the ultrasound probe;
synchronously acquiring tracking information including a plurality of tracking frames indicative of motion of the ultrasound probe from an inertial measurement unit coupled to the ultrasound probe;
determining a similarity value based upon a comparison of at least two ultrasound image frames of the plurality of ultrasound image frames;
computing whether the similarity value ($C_{frame}$) is less than a similarity threshold value ($C_{thresh}$); and
selecting first or second pose estimation methods for the ultrasound probe each different from each other based upon the results of the computation of whether the similarity value ($C_{frame}$) less than the similarity threshold value ($C_{thresh}$).

10. The method of claim 9, further comprising an act of selecting the first pose estimating method when it is determined that the similarity value ($C_{frame}$) is less than the similarity threshold value ($C_{thresh}$).

11. The method of claim 10, wherein the first pose estimating method determines pose by integrating the tracking information from the IMU, and thereafter stores the results in a memory of the system.

12. The method of claim 9, further comprising an act of selecting the second pose estimating method when it is determined that the similarity value ($C_{frame}$) is not less than the similarity threshold value ($C_{thresh}$).

13. The method of claim 12, wherein the second pose estimating method further comprises an act of determining pose based upon an image-based bias correction of integrated tracking information.

14. The method of claim 9, further comprising an act of determining pose in accordance with the selected pose estimation method and rendering the determined pose on a rendering device.

15. A non-transitory computer readable medium comprising computer instructions which, when executed by a processor, configure the processor to perform the acts of:
acquiring ultrasound image information including a plurality of ultrasound image frames from the ultrasound probe;
synchronously acquiring tracking information including a plurality of tracking frames indicative of motion of the ultrasound probe from an inertial measurement unit coupled to the ultrasound probe;
determining a similarity value based upon a comparison of at least two ultrasound image frames of the plurality of ultrasound image frames;
computing whether the similarity value ($C_{frame}$) is less than a similarity threshold value ($C_{thresh}$); and
selecting first or second pose estimation methods for the ultrasound probe each different from each other based upon the results of the computation of whether the similarity value ($C_{frame}$) less than the similarity threshold value ($C_{thresh}$).

16. The computer instructions of claim 15, further comprising an act of selecting the first pose estimating method when it is determined that the similarity value ($C_{frame}$) is less than the similarity threshold value ($C_{thresh}$).

17. The computer instructions of claim 16, wherein the first pose estimating method determines pose by integrating the tracking information from the IMU, and thereafter stores the results in a memory of the system.

18. The computer instructions of claim 15, further comprising an act of selecting the second pose estimating method when it is determined that the similarity value ($C_{frame}$) is not less than the similarity threshold value ($C_{thresh}$).

19. The computer instructions of claim 18, wherein the second pose estimating method further comprises an act of determining pose based upon an image-based bias correction of integrated tracking information.

20. The computer instructions of claim 15, further comprising an act of determining pose in accordance with the selected pose estimation method and rendering the determined pose on a rendering device.

* * * * *